(12) United States Patent
Hendriks et al.

(10) Patent No.: US 11,097,436 B2
(45) Date of Patent: Aug. 24, 2021

(54) FRICTION CONTROL DEVICE AND METHOD

(71) Applicant: KONINKLIJKE PHILIPS N.V., Eindhoven (NL)

(72) Inventors: Cornelis Petrus Hendriks, Eindhoven (NL); Daan Anton Van Den Ende, Breda (NL); Achim Hilgers, Alsdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 140 days.

(21) Appl. No.: 16/309,127

(22) PCT Filed: Jun. 12, 2017

(86) PCT No.: PCT/EP2017/064212
§ 371 (c)(1),
(2) Date: Dec. 12, 2018

(87) PCT Pub. No.: WO2017/220352
PCT Pub. Date: Dec. 28, 2017

(65) Prior Publication Data
US 2020/0070373 A1    Mar. 5, 2020

(30) Foreign Application Priority Data
Jun. 20, 2016  (EP) .................................. 16175190

(51) Int. Cl.
*B26B 19/38*   (2006.01)
*A61B 5/00*   (2006.01)
*H01L 41/193*   (2006.01)

(52) U.S. Cl.
CPC ............ *B26B 19/388* (2013.01); *A61B 5/442* (2013.01); *B26B 19/3886* (2013.01); *H01L 41/193* (2013.01)

(58) Field of Classification Search
CPC . B26B 19/388; B26B 19/3886; H01L 41/193; H01L 41/0986; A61B 5/442
See application file for complete search history.

(56) References Cited

U.S. PATENT DOCUMENTS 9,401,248 B2 *  7/2016  Brokken ................. G06F 3/016
10,309,377 B2 *  6/2019  van den Ende ....... H01L 41/042
(Continued)

FOREIGN PATENT DOCUMENTS

| EP | 2385562 A1 | 11/2011 |
|---|---|---|
| JP | 2002-218773 A | 8/2002 |
| JP | 2011-030375 A | 2/2011 |
| WO | 2016091706 A1 | 6/2016 |

OTHER PUBLICATIONS

Tsai and Cheng, "The Effect of Friction Reduction in the Presence of in-plane Vibrations" Arch Applied Mechanics (2006) 75: 164-176.

(Continued)

*Primary Examiner* — Hwei-Siu C Payer
(74) *Attorney, Agent, or Firm* — Schott, P.C.

(57) ABSTRACT

A friction control device (44) is adapted to induce a lateral strain (or stretching) within a human tissue surface to which the device is applied, in order thereby to reduce the static friction between the device and the human tissue surface. The strain is induced by means of an actuator arrangement adapted to effect a relative separation of a plurality of contact surface regions (40) of the device, such that when said regions are pressed onto the receiving surface, the relative separation induces a strain in at least the region of the receiving surface falling between the locations of the applied regions. The extent of separation matches or exceeds the minimum extent necessary to overcome static friction.

18 Claims, 5 Drawing Sheets

(56) References Cited

U.S. PATENT DOCUMENTS

| | | |
|---|---|---|
| 2013/0030329 A1 | 1/2013 | Zumeris et al. |
| 2013/0101804 A1 | 4/2013 | Brokken et al. |
| 2014/0349075 A1* | 11/2014 | Hendriks ............ B29C 37/0053 |
| | | 428/156 |
| 2015/0090544 A1 | 4/2015 | Gandhi |
| 2016/0129602 A1 | 5/2016 | Mintz et al. |
| 2017/0325566 A1 | 11/2017 | Fraklin et al. |
| 2018/0102717 A1* | 4/2018 | Hendriks .............. H01L 41/042 |
| 2018/0108827 A1* | 4/2018 | Hakkens ............. H01L 41/1132 |
| 2018/0248497 A1* | 8/2018 | Hendriks .............. H01L 41/193 |
| 2018/0254404 A1* | 9/2018 | Ubachs ..................... F03G 7/00 |
| 2019/0123258 A1* | 4/2019 | Hilgers ................. H01L 41/107 |
| 2019/0312193 A1* | 10/2019 | Pelssers ................ H01L 41/042 |
| 2020/0070373 A1* | 3/2020 | Hendriks ............. B26B 19/388 |

OTHER PUBLICATIONS

Popov et al., "Influence of Ultrasonic In-Plane Oscillators on Static and Sliding Friction and Intrinsic Length Scale of Dry Friction Processes" Tribology Letters (2010) 39: 25-30.
Starcevic and Filippov, "Simulation of the Influence of Ultrasonic in-plane Oscillations on Dry Friction Accounting for Stick and Creep", Physical Mesomechanics (2012), 15(3): 330-332.
Kevin Gouder, "Turbulent Skin-Friction Reduction by Electroactive Polymer Surfaces . . . " abstract DFD08 Meeting of the American Physical society, 2008.

\* cited by examiner

FRICTION CONTROL DEVICE AND METHOD

CROSS-REFERENCE TO PRIOR APPLICATIONS

This application is the U.S. National Phase application under 35 U.S.C. § 371 of International Application No. PCT/EP2017/064212, filed on Jun. 12, 2017, which claims the benefit of EP Patent Application No. EP 16175190.4, filed on Jun. 20, 2016. These applications are hereby incorporated by reference herein.

FIELD OF THE INVENTION

This invention relates to devices and methods for controlling friction across a contact interface, and in particular for reducing friction across an interface with human tissue.

BACKGROUND OF THE INVENTION

Gliding of a device against human tissue can be hindered by stiction (static friction) caused by local surface pinnings Local surface pinnings are interlocking or adhering surface roughness asperities which are responsible for frictional adhesion between two contacting surfaces. Adhesion between surfaces occurs due to a number of factors including bonds forming across the interface, mechanical interlocking, and often capillary effects. Interlocking surface asperities of two surfaces (surface pinnings) results in local adhesion regions between the two surfaces.

Smooth gliding of a device over an area of human tissue may be desirable for many applications. One particular field where this is desirable is that of medical or personal care devices, where smooth gliding over human tissue is of particular importance.

Where static friction is left uncontrolled, this can lead to the necessity to apply large lateral forces to contacting tissue, and induce significant displacement of the tissue, before slip or glide of the device over the tissue can be achieved. Often, there may also occur the phenomenon of 'stick-slip', wherein the motion of the device over the tissue is consistently arrested by local maxima of static friction, and requires re-application of large forces to re-commence gliding. The result is effectively the application of a large oscillating force to the tissue surface as the device is moved across it.

These phenomena typically have a negative influence on both the functionality and efficiency of the device, and also the comfort of the device to a user or a patient to whom the device is being applied. There may result tissue damage or irritation for example.

One common means to overcome the problems induced by stiction and to enable smooth gliding is to lubricate the contact surface by means of a wet hydrophilic coating or a lubricant. However, wet solutions are not always practical, particularly in the case of electrical personal care devices applied to skin, where introduction of water may be hazardous or may impede performance (e.g. electric shavers). Also, in some cases, the elimination of tissue stretching altogether is not desired. Rather simultaneous local stretching in combination with smooth global guiding may be the desired object. For instance, in the case of shavers, some local controlled stretching of skin may improve the performance of the device. Also, for certain catheter procedures, insertion may require smooth gliding, whereas aspects of the treatment itself may benefit from fixation of tissue induced by static friction.

A number of means are known in the art for controlling dynamic friction, some of which are based upon the concept of inducing in-plane and/or out of plane periodic deformations within a contacting surface. The abstract for the DFD08 Meeting of The American Physical Society, Gouder, K. Morrison, J. for instance discloses application of such a concept in reducing friction drag across a turbulent boundary layer. However, this method is directed exclusively to use in reducing drag i.e. dynamic friction with respect to a fluid, and has limited utility in reducing static friction across a boundary between two solid layers.

Document US 2013/0030329 discloses a means for reducing dynamic friction between a medical device and human tissue by inducing surface acoustic wave vibrations along the surface of the medical device.

Both of these disclosed methods are based on the concept of propagating travelling waves or vibrations along the surface of a contacting plane of a device. However, such methods require inducing vibrations within the body of the entire device, in order to achieve the vibrations along the contacting surface. This results in a high power consumption, which increases costs, and may also increase the weight of a device (if a larger battery is required) or reduce performance (if the device lasts for a shorter period of time before a battery drains). Such solutions can also cause significant discomfort for a user, since vibrations are felt throughout the device, and are not directed exclusively to the contacting surface.

Additionally, such an approach to friction reduction offers limited flexibility in terms of controlling the degree of friction reduction or adjusting for different surface materials. Localized control at different surface regions across the device is also not possible—since the same vibrations are naturally propagated across the entire contacting surface (and indeed the entire device).

Improved means for controllably reducing static friction between an application surface of a device and a receiving surface of an external body are therefore desired.

SUMMARY OF THE INVENTION

The invention is defined by the claims.

According to an aspect of the invention, there is provided a friction control device for application to a human tissue receiving surface, the device adapted to establish an interface with said receiving surface having a reduced static friction, the device comprising:

a contact surface arrangement comprising a plurality of contact surface regions for making contact with said receiving surface; and an actuator assembly adapted to control a relative separation of said contact surface regions in dependence upon an elasticity of the receiving surface and one or more surface properties of the receiving surface, such that the extent of separation matches or exceeds that which can be applied to the receiving surface via the contact surface regions without static frictional forces across the interface being overcome.

The provided friction control device is adapted to be applied to a region of human tissue, whereupon the separation of applied contact surface regions induces a strain within the receiving surface to which it is applied. The strain is induced at least across the area of the receiving surface spanned by the plurality of surface regions, but may extend beyond to some extent.

The magnitude of the strain induced is naturally dependent upon the magnitude of the relative separation induced between the contact surface regions. The extent of this separation is selected to induce a corresponding strain in the receiving surface which exceeds that which can be supported by the contacting surface regions without static frictional forces between the regions and the receiving surface being overcome.

The particular degree of relative separation necessary to arrive at this state is dependent both upon the elastic properties of the human tissue receiving surface and upon certain material properties of the surface of the tissue layer (such as degree of roughness or smoothness).

Inducing a strain in the receiving surface naturally requires application of a lateral force to the receiving surface via the contact surface regions (or application of a force having a lateral component). The contact surface regions are only adapted to apply such a lateral force while they remain statically adhered to the receiving surface by static friction forces. As greater strain is induced in the layer though the separation of the contact regions, a greater stress and concurrent greater tensile force is induced across the layer, which must be resisted by the surface regions in order to maintain the separation.

At a certain point, the lateral force needed to be applied to resist the tensile force built up in the receiving surface exceeds the static frictional forces holding the contact surface regions adhered to the receiving surface. At this point, 'slip' occurs—a state is obtained in which further application of the lateral force would cause the surface regions (or indeed any other similarly applied contacting bodies) to slide over the receiving surface. The degree of separation required to achieve this state is the degree of strain provided by embodiments of the present invention.

At the point where the induced separation exceeds that which can be transferred to the receiving surface via the contact surface regions without overcoming static frictional forces, interfacial surface pinnings are broken and/or are prevented from properly forming. As a result, static friction between the strained receiving surface and any surface with which it makes contact (while this degree of strain/stretching is maintained) is significantly reduced.

The plurality of contact surface regions may in examples refer to different regions of a single unitary surface, or may refer to surfaces of a plurality of distinct surface components. In the former case, the plurality of surface regions may be taken to refer to a plurality of arbitrarily defined regions of the surface. These arbitrary regions may be defined to be contiguous or non-contiguous.

The breaking of local surface pinnings may be achieved where the contact surface regions are separated in dependence upon a stretching capability of the receiving surface such that the extent of relative separation is greater than that which can be accommodated by the stretching of the receiving surface.

The actuator assembly controls a relative separation of the contact surface regions. The relative separation is controlled to increase from a first initial relative separation to a second, larger relative separation. Each of the plurality of surface regions may be controlled to increase its relative separation with respect to every other surface region. In this way, a stretching across the whole area covered by the plurality of surface regions is achieved.

In accordance with at least one set of examples, the actuator assembly is adapted to control the relative separation of the contact surface regions in dependence upon the coefficient of static friction between the contact surface regions and the receiving surface, and the modulus of elasticity of the receiving surface. The relative separation may be increased in proportion to the quotient of these two values. This value provides one measure of the strain that it is necessary to induce in the receiving surface in order to break the surface pinnings and initiate slip (that is, initiate a condition in which static friction across the receiving surface is minimised). The value reflects a state in which the induced strain in the receiving surface is equal to, or just greater than, the static frictional force being exerted between the receiving surface and each of the plurality of surface portions.

The actuator assembly may in examples be adapted to control the relative separation between the surface regions so as to increase from a first separation distance to a second separation distance, wherein the ratio of the second distance to the first distance is:

between 1.001 and 1.01; or
between 1.01 and 1.1; or
greater than 1.1.

A value between 1.001 and 1.01 is particularly suited for inducing a state of slip on a moist skin.

A value between 1.01 and 1.1 is particularly suited for inducing a state of slip on normal skin.

A value greater than 1.1 is particularly suited for inducing a state of slip on dry skin.

In accordance with at least one set of examples, the plurality of surface regions may be comprised by a surface of a unitary flexible layer, said surface of the layer defining a plane, and wherein the actuator assembly is adapted to induce a lateral strain across said layer in a direction parallel with said plane, thereby actuating a separation of the plurality of surface regions.

According to this set of examples, the contact surface regions referred to may be considered notional, arbitrarily defined regions of the single unitary layer. The regions may be defined to be contiguous or to be spatially separated and may be of any size and of any plural number. By inducing a strain across the flexible unitary layer (i.e. expanding or stretching the layer), any arbitrarily defined regions of the layer will be induced to separate from one another. When the layer is applied in contact with a (human tissue) receiving surface, this expansion of the layer induces an exactly commensurate expansion of the receiving surface. The receiving surface follows the expansion of the flexible unitary layer. A (roughly) homogenous strain is induced in this case across the entire extent of the area of human tissue covered by the flexible unitary surface.

This induced strain in the human tissue receiving surface causes a breaking of the surface pinnings (as described above) and hence a reduction of the static friction force exhibited between the applied unitary surface and the receiving surface. According to an ideal model, the static friction force felt between these two contacting layers reduces to a value which is negligible, meaning that almost resistance-free (global) slip or gliding of the unitary surface over the human tissue layer is possible. By global slip is meant is a slipping, or translational motion, of the entire unitary surface relative to the receiving surface (as opposed simply to translational motion of two or more contact surface regions relative to the receiving surface).

Hence, once the separation between the surface regions has been effected, and the commensurate strain in the human tissue receiving surface induced, the entire unitary flexible layer may be shifted from a static state to a moving state, and moved or translated in any given direction over the human tissue receiving surface, without encountering significant resistive static frictional forces.

Moreover, as noted above, inducement of the lateral strain by the presently claimed method of relative separation of surface regions enables, in accordance with any embodiment of the invention, realisation of a substantially homogeneous strain across the entire area spanned by the contact surface regions. The strain is typically homogeneous both directionally and in terms of magnitude. Realization of a homogeneous strain is particularly important in the case of reduction of static friction across relatively large area interfaces since any inhomogeneity could lead to localized maxima in shear resistance, leading to so-called 'stick-slip', wherein continuous motion of the contact surface arrangement over the receiving surface is impeded and motion must be restarted again. Hence the ability to realize a relatively homogeneous strain across a relatively wide interface area is a significant advantage of the present invention in terms of efficacy in countering static frictional resistance.

It is noted that the term 'lateral strain' is intended simply to mean an in-plane strain parallel with the unitary flexible layer. In other parts of the present disclosure, the term 'shear strain' may occasionally also be applied to refer to the same concept.

The induced strain across the unitary layer may be in one more directions parallel with a plane defined by the layer. The plane defined by the layer may be a plane defined by a major surface of the layer, and may be the plane defined by the surface of the layer comprising the plurality of contact surface regions. It may also refer more generally to a central lateral plane of the layer for instance.

According to one or more examples, the described process of straining the receiving surface may be repeated recurrently in order to enable the flexible unitary layer to be freely moved over the receiving surface, starting and stopping at will, and wherein each re-commencement of motion may be achieved with the same reduced or substantially eliminated static frictional force between the layer and the human tissue receiving surface. There may in some embodiments be provided a controller configured to detect cessation of motion (for instance by means of an operatively coupled motion detector), and to initiate separation of the surface portions in response. In other examples, there may be provided a controller configured to control a periodic separation of the surface portions.

In accordance with at least one set of embodiments, the actuator assembly may comprise one or more responsive material components adapted to deform in response to an electrical, thermal, magnetic or electromagnetic stimulus. Responsive materials (or 'smart materials'), are a well-known class of materials which are adapted to change or vary their shape in dependence upon the environment. This shape change may be utilised to provide actuation functionality.

In particular, the one or more responsive material components may, in some examples, be mechanically coupled to the flexible unitary layer and configured such that their deformation mechanically manipulates the flexible unitary layer to exhibit said lateral strain. For example the one or more reactive material components may be co-operatively configured so as to couple to two opposing ends of the flexible unitary layer, and to deform (in response to an appropriate stimulus) in such a way as to pull the two ends apart from one another and thereby induce the lateral strain across it. This represents just one example however, and any alternative suitable arrangement having the result of inducing a strain in the layer may also be considered.

According to a different set of examples, the actuator assembly may be incorporated within the unitary flexible layer, the layer being formed of a responsive material adapted to deform in response to an applied stimulus in order thereby to induce a lateral strain across the layer in one or more directions parallel with said plane, and consequently actuate a separation of the plurality of surface regions of the surface of the layer.

In these examples, external actuation components are not necessary to effect a separation of the contact surface regions. Rather, the flexible unitary layer is itself partially composed of responsive materials, and is adapted to respond to an appropriate stimulus by expanding or stretching in one or more directions parallel with the plane defined by the layer. Such a configuration may provide a more compact and/or lightweight solution, since dedicated actuation components are not required. This may enable a smaller form factor. It may also render the device simpler, faster and/or less expensive to manufacture. It may be easier to assemble or fabricate. It may allow for simpler control electronics.

According to a further set of examples, the actuator assembly may comprise one or more mechanical actuators adapted to manipulate the unitary flexible layer to induce a lateral strain across it in direction parallel with said plane defined by the layer. The mechanical actuators may for example be coupled to opposing ends of the layer, and configured to apply opposing forces so as to induce a strain across the layer, between the opposing ends. However, any other suitable arrangement may also be used. The mechanical actuators may not be coupled to the unitary layer for instance, or may be coupled to the layer at more central points.

Optionally, the actuator assembly may comprise an energy transmission mechanism adapted to receive as input an external source of kinetic energy and to transfer said kinetic energy into the one or more mechanical actuators. Such an arrangement is particularly suited to applications in which the friction control device is coupled or mounted to a contacting surface of a primary device or instrument which generates local motion or oscillations as part of its ordinary functioning. This might be the case for instance for a shaver or trimmer. Here, the oscillating motion of the shaver or trimmer blades might be partially harnessed by an energy transmission mechanism of the actuator arrangement to provide a source of kinetic energy to drive manipulation of the contact surface regions. This adaptation may also be applied in combination with any other embodiment described in this application. This effectively enables the main power source of the shaver or trimmer to be used to power the actuator arrangement without the need to provide electrical cables running between the two.

For any of the above-described examples, the actuator arrangement, whether it comprises responsive material components or mechanical actuators, may be configured to effect or induce a lateral strain across the flexible unitary layer in two orthogonal directions parallel to the plane defined by the layer.

In particular examples, the unitary flexible layer may be a rectangular layer. In other particular examples, it may define a closed, rounded shape, such as a circle, ellipse, or a non-regular rounded shape. The flexible unitary layer may in other examples take any particular shape or form including regular shapes or free-form shapes.

In accordance with a further set of embodiments, the contact surface arrangement may comprise surfaces of a plurality of spatially separated contact elements. The contact elements may be rigid elements featuring a planar or curved contact surface. The contact elements may be very small, micro-sized elements and may be configured and arranged to be movable with respect to one another in one or more directions. The actuator arrangement is configured to effect an increase in the separation distance between each of the contact elements. The contact elements may move apart from one another in a substantially homogenous manner.

Such an arrangement allows greater freedom in the choice of material for the contact surface regions. The material does not, unlike in previous examples, need to facilitate the dual function of flexible expansion and human tissue contact. This allows for greater choice. For instance, materials may be chosen which are hydrophilic or hydrophobic, or materials may be selected to provide a particular desired surface finish (i.e. having a particular roughness or smoothness).

In particular examples, the plurality of surface regions may be coupled or mounted to a major surface of a unitary flexible layer, the actuator arrangement being adapted to induce a strain across said layer in order thereby to effect a separation (increase in the relative separation) between the plurality of surface elements. The actuator arrangement may in this case comprise mechanical actuators or responsive material components adapted to provide an actuation function.

The actuator arrangement may comprise a layer of a responsive material adapted to deform in response to an electrical, thermal, magnetic or electromagnetic stimulus, the deformation inducing a lateral strain in the layer in a direction parallel with a plane defined by the layer, and wherein the plurality of contact elements are coupled to a surface of said layer such that the deformation of the layer induces the relative separation of the contact elements. Optionally, strain may be induced in two orthogonal directions parallel to the plane defined by the layer.

The actuator arrangement may comprise one or more mechanical actuators adapted to physically manipulate the plurality of contact elements in order to induce the relative separation between them.

In any of these examples, the contact elements may be arranged such that a spatial separation is maintained between all of the contact elements. In other examples, at least a portion of the contact elements may slide over one another. In further examples, the plurality of contact elements may be compliantly coupled to one another via an elastic coupling which strains with the relative separation of the elements. This may provide a convenient means of returning the elements to an initial configuration. It may speed up return of the elements in some examples.

Additionally, according to any of these examples, the skin contacting elements may be adapted such that the maximal induced separation between any two contacting elements is extremely small (for example <<0.1 mm). This would ensure that upon relative expansion of the elements (in order to induce skin stretching) so called 'doming' effects, wherein skin protrudes into the gaps in between elements, may be avoided. Such doming or protrusion can result in discomfort for a user, since, upon bringing the elements back together again, domed areas of skin can become trapped between neighbouring elements, resulting in pinching of the skin. By keeping maximal separation distance—and also maximal contact element outer extension—small enough, doming can be avoided.

In relevant above examples, reactive materials have been described in a general sense. However, in more particular examples, an electroactive polymer material may be used as the responsive material.

According to at least one set of embodiments, the friction control device may further comprise a controller adapted to control the actuator assembly to actuate a periodic relative separation between the surface portions, such that the relative separation varies periodically over time. By periodically actuating the surface regions to separate from one another (increase their relative separation distance) at a suitable frequency, one is able to allow for relatively arbitrary stop-start global motion of the contact surface arrangement over an area of human tissue, while ensuring reduced static friction between the surface arrangement and the tissue whenever motion is stopped.

In accordance with one set of examples, the friction control device may further comprise a controller adapted to control the actuator assembly to actuate a relative separation between the surface regions of a magnitude dependent upon the coefficient of static friction between the receiving surface and the contact surface regions and further dependent upon the elastic modulus of the receiving surface. The device may further comprise one or more sensors for detecting an elastic modulus of the human tissue receiving surface or for detecting one or more other parameters suitable for determining elastic modulus. The device may also comprise sensors adapted to detect one or more surface parameters, suitable in particular for determining a coefficient of static friction between the receiving surface and the contact surface regions.

In accordance with one or more examples, the device may further comprise a sensor for detecting contact of the device with the human tissue receiving surface. There may further be a controller adapted to initiate separation of the contact surface regions in response to detection of human tissue contact.

According to a further aspect of the invention, there is provided a shaver or trimmer comprising a head portion for contacting a user's skin, the head portion comprising a friction control device as claimed in any preceding claim.

According to another aspect of the invention, there is provided a method of controlling static friction across an interface between a contact surface arrangement and a receiving surface of an external body, the contact surface arrangement comprising a plurality of contact surface regions for making contact with said receiving surface of an external body, the method comprising:

actuating a relative separation of said contact surface regions in dependence upon an elasticity of the receiving surface and one or more surface properties of the receiving surface, such that the extent of separation matches or exceeds that which can be applied to the receiving surface via the contact surface regions without static frictional forces across the interface being overcome.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a friction control device adapted to induce a lateral strain (or stretching) within a human tissue surface to which the device is applied, in order thereby to reduce the static friction between the device and the human tissue surface. The strain is induced by means of an actuator arrangement adapted to effect a relative separation of a plurality of contact surface regions of the device, such that when said regions are pressed onto the receiving surface, the relative separation induces a strain in at least the region of the receiving surface falling between the locations of the applied regions.

As explained above, the device has particular application in the case of skin contact devices, where controlled reduction of static friction may reduce skin damage or skin irritation. Surface static friction at an interface with skin is typically high, requiring application of relatively large forces to overcome it, and also inducing an undesirably large displacement of skin and underlying surface tissue. Surface abrasion caused in overcoming the static friction and initiating motion of the device may cause skin irritation. The large displacement of skin and underlying tissue may cause damage or inflammation of the skin.

Figure 1:
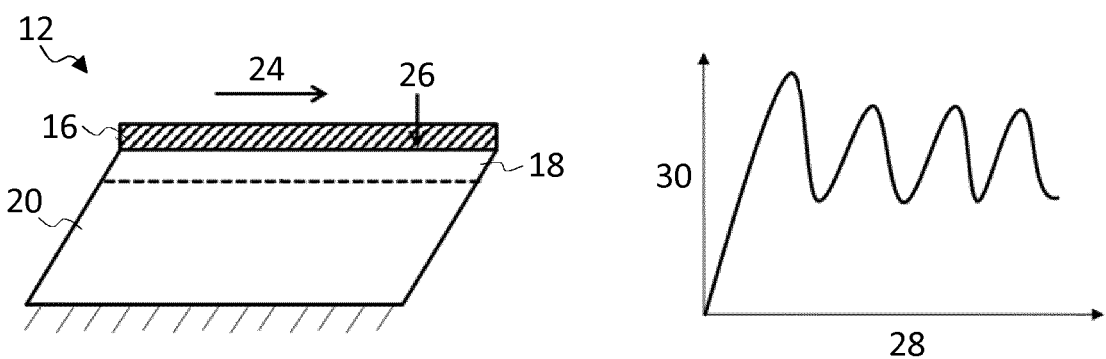
FIG. 1 schematically illustrates application of lateral force to a human tissue layer and associated static friction forces encountered.

FIG. 1 schematically illustrates the application of a lateral force 24 to a body of human skin tissue 18, 20 by means of a rigid contacting surface 16, in order to move the surface over the body of tissue. As shown, the motion of the contacting surface 16 over the human tissue is being resisted by static frictional forces acting across the interface 26 between the two. The rigid contacting surface 16 makes direct contact with the stiff epithelium layer 18. As illustrated, the lateral force applied induces a displacement of the epithelium 18 in the direction of the applied force 24, which causes a corresponding stretching or straining of the body of soft tissue 20 lying beneath.

The magnitude of resistive frictional force 30 applied across the interface 26 as a function of time 28 (or of gliding distance of the rigid contacting surface 16) is illustrated by the graph shown on the right hand side of FIG. 1. As shown, commencement of initial motion of the rigid contacting surface 16 requires application of a large lateral force to the epithelium 18 in order to fully overcome resistive static frictional forces. However, as can further be seen from the graph, continuous motion or gliding of the contacting surface 16 over the epithelium is impeded by the continuing return of surface frictional forces, which oscillate in magnitude as the rigid contacting layer is forced repeatedly to stop and start. Each stoppage requires re-application of the initial large force in order to overcome the frictional resistance and to re-commence motion. This effect is known as 'stick-slip'.

Figure 2:
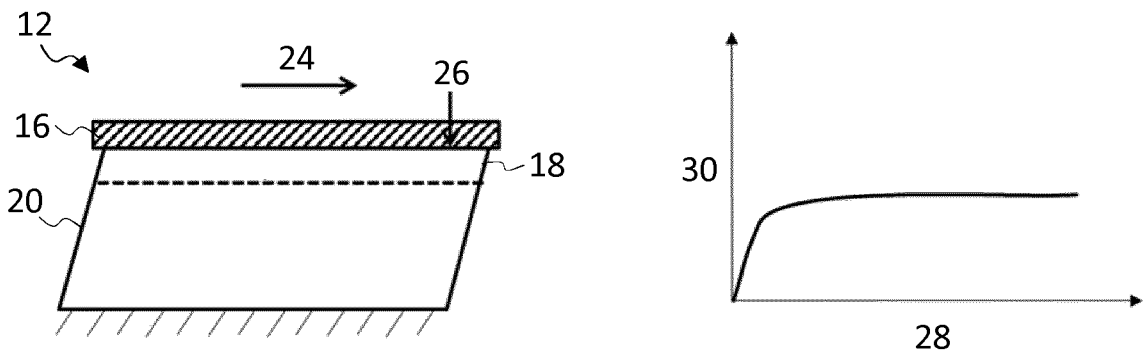
FIG. 2 schematically illustrates application of lateral force to a human tissue layer and associated static friction forces encountered, wherein the layer has been stretched in accordance with embodiments of the invention.

By contrast, FIG. 2 schematically illustrates the application of a lateral force to a body of human tissue 18, 20 by means of a contacting surface 16, wherein the receiving surface of the epithelium 18 is in a state of being stretched in accordance with embodiments of the present invention in order to achieve a state of slip. The stretching in this case may be assumed to be achieved through an expansion of contacting surface 16 (as described in relation to a number of examples above). However, the demonstrated effect is not limited to such a case, and any means of stretching may equally be used.

As shown in the corresponding graph of FIG. 2, the magnitude of resistive frictional forces 30 opposing initiation of motion in this case (where the surface is being strained) is significantly reduced, meaning that motion may be achieved through application of an initial force of significantly reduced magnitude. This reduces the likelihood, or at least the acuity, of any consequent tissue damage or skin irritation.

The graph of FIG. 2 also illustrates that, by contrast with the scenario of FIG. 1, the resistive frictional forces, once overcome to initiate motion, do not continue to recurrently return but rather remain at a constant (low) level. As a result, the phenomenon of stick-slip is avoided.

Although FIGS. 1 and 2 illustrate the problem overcome by the invention by way of reference to a body of skin 18, 20, it is to be understood that the invention is not limited to use with skin tissue, and it is fully anticipated that the invention may be applied with equal advantage to any other body of human tissue. This may include for instance internal tissues, such as tissues of artery, oesophageal, or intestinal walls, or of internal organs.

Figure 3:
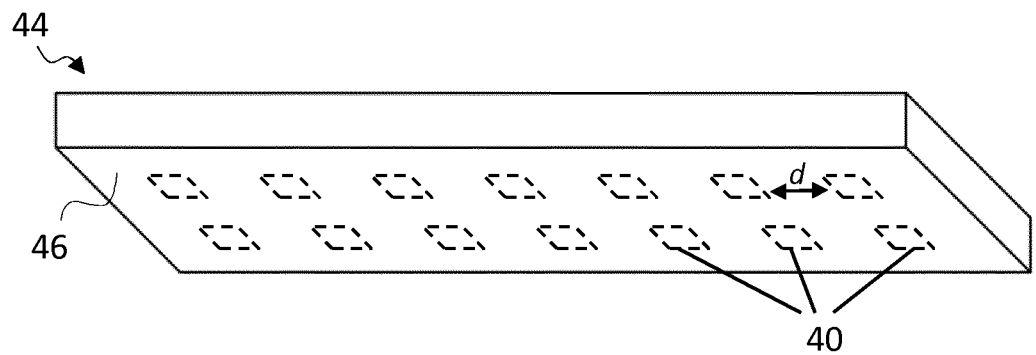
FIG. 3 schematically depicts an example unitary flexible layer comprising a plurality of contact surface regions as incorporated within embodiments of the present invention.
Figure 4:
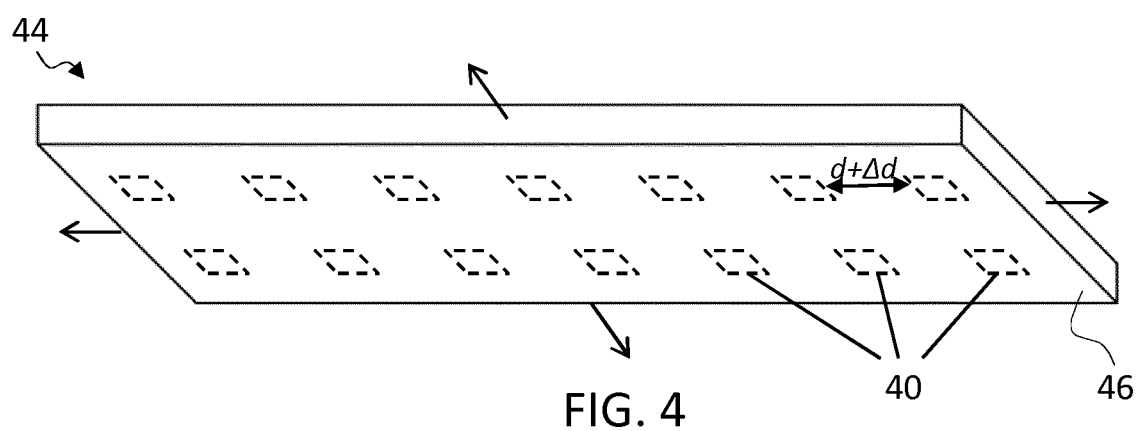
FIG. 4 schematically depicts an example unitary flexible layer which has stretched to separate the plurality of contact surface regions.

FIGS. 3 and 4 schematically illustrate a first example friction control device in accordance with one or more embodiments of the invention. The device comprises a unitary layer 44 formed of a flexible material which is adapted to accommodate lateral stretching outwards from the layer along directions parallel with the plane defined by a lower major surface 46 of the layer.

The lower major surface 46 of the layer defines a contact surface for making contact with a receiving surface of human tissue. The contact surface 46 may be understood as being notionally divided into an arrangement of arbitrarily defined contact surface regions 40. The contact surface regions in this case are defined so as to form a regular array of spatially separated regions.

FIGS. 3 and 4 respectively illustrate the unitary layer 44 in an initial, undeformed state, and in a later, deformed (stretched) state. As shown, in the later stretched state, the separation distance d between each of the plurality of contact surface regions 40 is increased (to d+Δd). When this stretching of the layer is induced while the layer is being applied to a receiving surface of a body of human tissue, the relative separation of the plurality of contact surface regions induces a corresponding stretching of the receiving surface. The magnitude of relative separation is controlled so as to induce a strain in the receiving surface of a magnitude equal to or greater than that which can be accommodated before static friction forces between the two surfaces are overcome (and a state of slip is hence achieved).

As discussed above, the magnitude of relative separation of the contact surface regions 40 necessary to induce a state of slip across a receiving surface 18 may be understood as depending upon both the elasticity of the human tissue receiving surface and the coefficient of static friction between the receiving surface and the contact surface regions 40.

The necessary amount of separation may be estimated by means of a simple (idealised) model which describes the human tissue receiving surface 18 as an elastic layer having modulus of Elasticity E.

Figure 5:
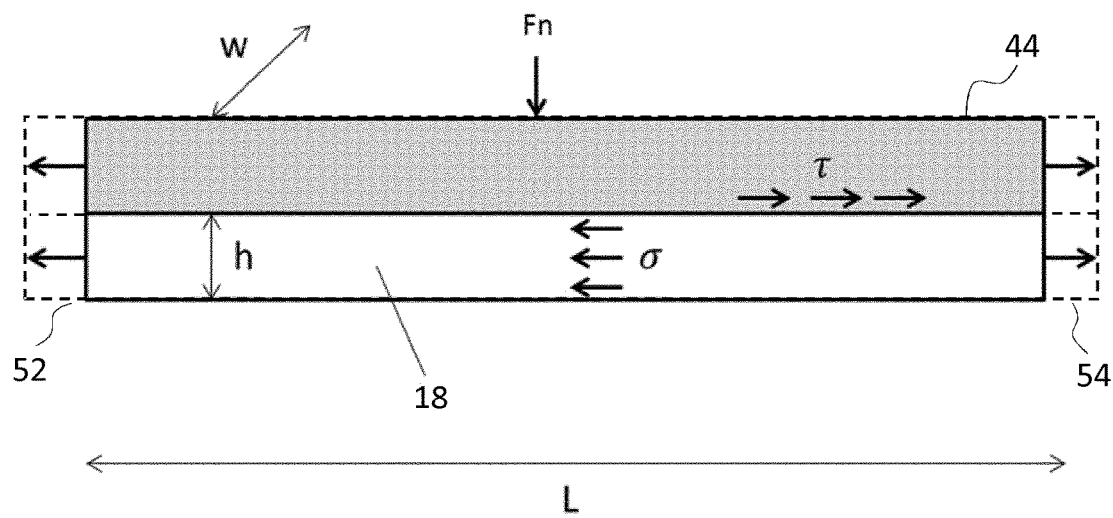
FIG. 5 schematically illustrates a modelled physical interaction between a contact surface of a flexible contact layer and a human tissue receiving surface.

The model as applied to the embodiment of FIGS. 3 and 4, in which the contact surface regions are comprised by a single flexible unitary layer 44, is illustrated in FIG. 5. Here, the flexible unitary layer 44 is similarly modelled as an elastic layer, making contact with the human tissue receiving surface 18 across an interface having coefficient of static friction $\mu_s$, and being loaded with normal application force $F_n$.

The unitary layer is modelled as having an applied shear (in-plane) strain ε. It is assumed that both the unitary layer 44 and the receiving surface 18 may only deform in plane (i.e. in directions parallel with the plane defined by/parallel with the major surfaces of the layers). Due to the interfacial static friction force between the two layers, the human tissue receiving surface follows the expansion of the flexible unitary layer 44, thereby similarly inducing in the receiving surface a strain ε.

The receiving surface continues to follow the expansion of the flexible unitary layer only so long as the shear tensile force built up within the receiving surface does not exceed the static frictional force exerted across the interface between the two layers. As soon as the tensile force exceeds the magnitude of the frictional forces, slip will occur, since the elastic tensile force built up in the layer 18 will overcome the frictional force and enable the layer to simply slide over the surface of the expanding unitary layer.

The human tissue receiving surface 18 is modelled as having induced stress σ. The corresponding tensile force $F_T$ exhibited across the layer may therefore be taken as $F_T$=σhw, where h and w are the height and width respectively of receiving surface 18. The exhibited static frictional force may be taken to have value $F_\mu = \mu_s F_n$. The requirement for slip may therefore be stated as:

$$\sigma h w > \mu_s F_n \quad (1)$$

Since the human tissue receiving surface 18 has modulus of elasticity E, and since E=σ/ε, inequality (1) may be expressed as:

$$\varepsilon > \frac{\mu_s F_n}{Ewh} \quad (2)$$

Inequality (2) describes the required strain to be induced within the human tissue receiving surface 18 in order to initiate slip as a function of elasticity of the receiving surface and of the coefficient of static friction between the receiving surface and an expanding contact surface arrangement 44.

The model is based on the simplifying assumption that the strain ε and shear stress σ are applied roughly homogenous across the human tissue receiving surface, and similarly that the strain is induced roughly homogenously across the flexible unitary layer.

It is noted that inequality (2) can also be derived by using the fact that, in the case of static friction, the frictional force $\mu_s F_n$ is equal to the tensile force τwL induced in the flexible unitary layer 44. Hence inequality (1) may be expressed as σhw>τwL. One may then apply the fact that σ=Eε and τ=$\mu_s F_n$/wL. Inequality (2) then directly follows.

The model also assumes that the elastic modulus of the flexible unitary layer 44 is significantly greater than that of the human tissue receiving surface 18. In practice, it is assumed that the unitary layer 44 has elastic modulus of at least an order of magnitude greater than that of the receiving surface 18. The disparity in stiffness of the two layers ensures that the greater stress for a given induced strain is always induced in the flexible unitary layer, and the lesser stress in the human tissue receiving surface. This ensures a mechanically stable system at the point of slip, since no excess stress is built up in either layer—where by 'excess stress' is meant a stress greater than the product of the elastic modulus of the layer and the strain induced within it. Were the human tissue layer to have greater stiffness than the expanding layer 44, then excess stress would be built up in the expanding layer, potentially resulting in the occurrence of a sudden rapid expansion of the layer at the point of slip, as the excess (outwardly directed) tension is released.

Despite this however, it is still possible to achieve the desired breaking of surface pinnings and reduction of static friction in the case that the flexible unitary layer 44 has a lower modulus of elasticity than the human tissue receiving surface 18. In this case however, in determining the condition for slip, the elastic modulus E' and dimensions w', h' of the flexible unitary layer should be considered instead of those of the human tissue receiving surface. In this case, the stress σ' built up within the flexible unitary layer provides a limiting condition, rather than the strain. The result is the following condition for initiation of slip:

$$\sigma' = \varepsilon E' > \frac{\mu_s F_n}{w' h'} \quad (3)$$

It is emphasised that although the model above has been framed in terms of expansion of a single unitary layer 44 comprising the plurality of contact surface regions 40, the model is by no means limited to this embodiment. It may also be applied to embodiments in which the plurality of contact surface regions 40 are comprised by a plurality of spatially separated contact elements for instance. (Such an embodiment will be described in more detail further below).

The model may be generalised therefore, and re-framed in terms of the required increase in the separation distance d between contact surface regions 40 of a friction control device understood in its broadest since. Since the separation of the contact surface regions exactly mirrors the straining of the receiving surface (at least while static friction forces are not overcome), the strain ε may equally be understood as referring to the proportional change in separation distance $\Delta d_{prop}$ between each of (at least a subset of) the plurality of contact surface regions 40. By proportional change in separation is meant the absolute change in separation distance divided by the original separation distance:

$$\varepsilon \sim \Delta d_{prop} = \frac{\Delta d}{d_i} = \frac{d_f - d_i}{d_i} \quad (4)$$

where $\Delta d$=absolute change in separation distance, $d_f$=final separation distance, and $d_i$=initial separation distance.

The typical values of strain which it would be required to induce in a human tissue receiving surface to initiate a condition of slip are values which are readily achievable by means of real-world materials, including responsive materials.

Figure 6:
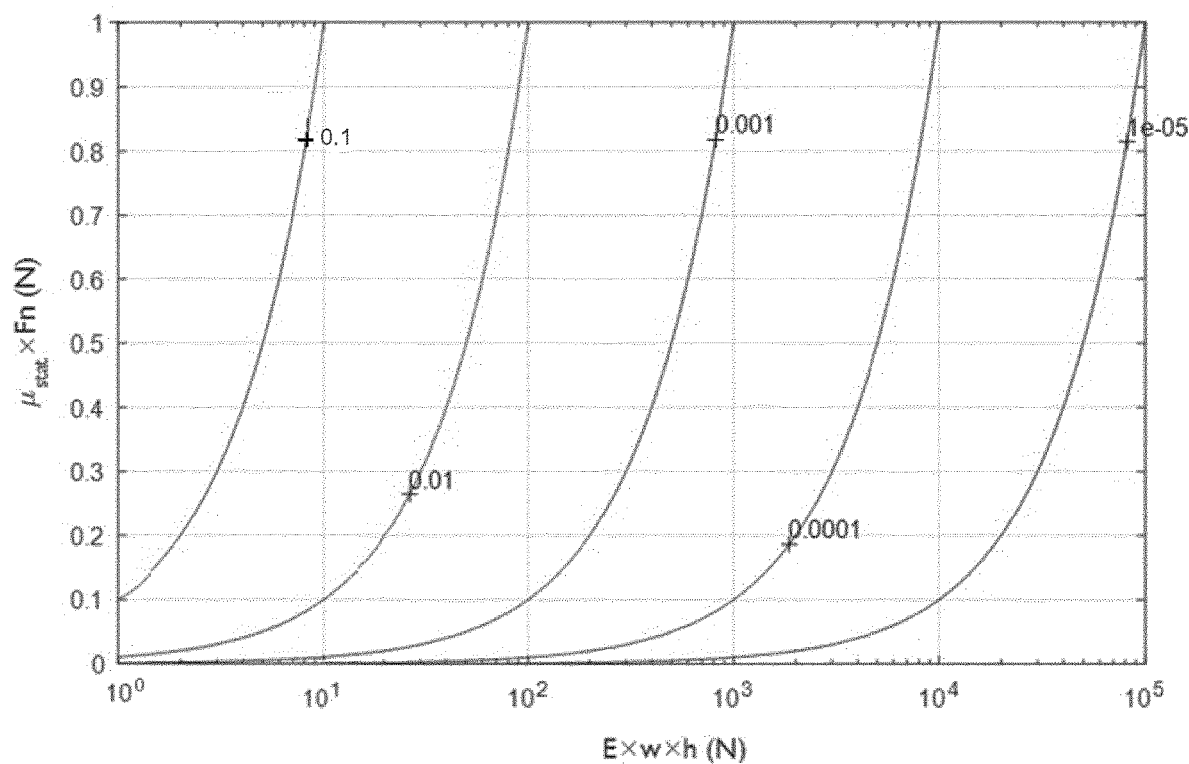
FIG. 6 shows a graph illustrating the necessary strain required be induced within human tissue receiving surface in order to initiate a state of slip.

FIG. 6 shows a graph illustrating a number of example strain values which it might be necessary to induce, each corresponding to a particular spectrum or band of assumed physical and geometrical conditions. The y axis represents a frictional resistance force exerted across the material interface—equal to $\mu_s F_n$ (Netwons). The x-axis represents an elastic resistance force within the receiving surface—equal to Ewh (Netwons). Each curve on the graph corresponds to a particular (example) strain value which would be necessary for inducing slip for any of the particular physical scenarios represented by points along that line. This follows from equation (2) above, which shows that the required strain in any scenario is greater than $\mu_s F_n$/Ewh, i.e. the gradient of any line or curve in the graph of FIG. 6.

The curves indicated are shown purely by way of illustration, as strain values which it would be realistic and feasible to achieve using common materials, including common responsive materials. Of course, any number of different curves could also be added to the graph, lying in-between those shown, each to represent a different value of feasible strain. The particular curves shown are merely demonstrative of the concept.

From left to right, the first curve (or band) corresponds to scenarios for which the required strain to induce slip would be 0.1, the second to scenarios for which required strain is 0.01, the third for which required strain is $1 \times 10^{-3}$, the fourth to strain of $1 \times 10^{-4}$ and the fifth to strain of $1 \times 10^{-5}$.

By way of example, a typical layer of moist skin epidermis, of elasticity $E=10^6$ Pa, and of cross-sectional area=$1 \times 10^{-4}$ m, has elastic resistance Ewh (taking w*h=cross sectional area) of 1 N. Using the graph of FIG. 6, it can be seen that slip could be induced across such a layer at an induced strain of 0.1 (for example) if $\mu_s F_n$ at the material interface had a value of 0.1 N. Equally, slip could be induced at an induced strain of 0.01 (again, for example), were the value of $\mu_s F_n$ for the interface equal to 0.01 N.

These values of $\mu_s F_n$ are entirely feasible and realistic in a real-world scenario, as are the strain values of 0.1 and 0.01.

To give a second example, a typical layer of dry skin epidermis, of elasticity $E=10^9$ Pa, and of cross-sectional area=$1 \times 10^{-7}$ m, has elastic resistance Ewh (taking w*h=cross sectional area) of 100 N. From the graph, it can be seen that slip could be induced in this scenario with an induced strain of 0.001 if $\mu_s F_n$=0.1, or a strain of 0.01 if $\mu_s F_n$=1, or a strain of 0.0001 if $\mu_s F_n$=0.01. Again, these numbers are purely exemplary and given by way of illustration of the concept only.

As discussed in preceding sections, the stretching or expansion of the flexible unitary layer 44 may be achieved according to a number of different mechanisms.

In accordance with at least one set of embodiments, the layer 44 may comprise an Electroactive polymer (EAP) material which is adapted to expand in response to the application of an electrical stimulus. Electroactive polymers (EAPs) are an emerging class of materials within the field of electrically responsive materials. EAPs more broadly may be used as both sensors and actuators and can easily be manufactured into various shapes allowing easy integration into a wide variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

An EAP device generally can be used in any application in which a small amount of movement of a component or feature is desired, based on electric actuation. Similarly, the technology can be used for sensing small movements. This invention relates in particular to actuators.

The use of EAPs enables functions which were not possible before, or offers a big advantage over common actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes). Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is conjugated/ conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

Figure 7:
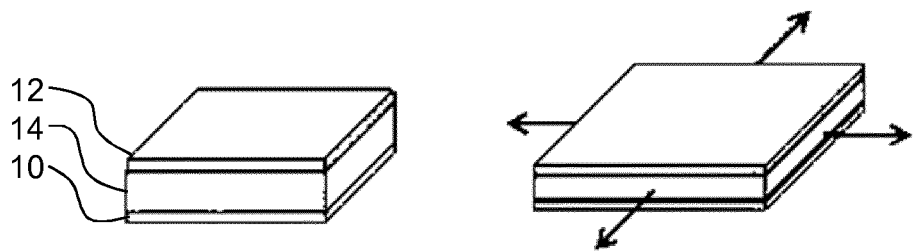
FIG. 7 schematically illustrates an example electroactive polymer layer which is clamped.
Figure 8:
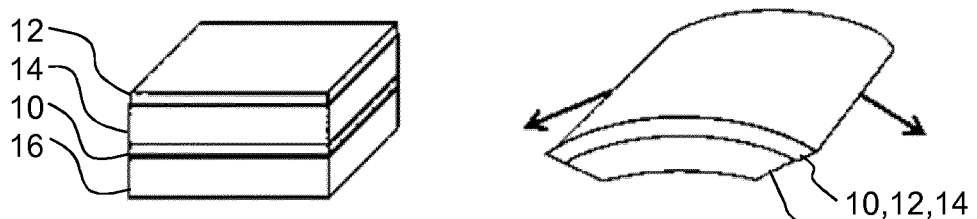
FIG. 8 schematically illustrates an example electroactive polymer layer which is not clamped.

FIGS. 7 and 8 show two possible operating modes for an EAP device.

The device comprises an electroactive polymer layer 14 sandwiched between electrodes 10, 12 on opposite sides of the electroactive polymer layer 14.

FIG. 7 shows a device which is not clamped. A voltage is used to cause the electroactive polymer layer to expand in all directions as shown.

FIG. 8 shows a device which is designed so that the expansion arises only in one direction. The device is supported by a carrier layer 16. A voltage is used to cause the electroactive polymer layer to curve or bow.

The example of FIG. 8 may also be clamped to provide a layer which expands in-plane but in a single direction only.

Together, the electrodes, electroactive polymer layer, and carrier may be considered to constitute the overall electroactive polymer structure.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

The EAP may hence be adapted to deform in response to application of the electrical stimulus in such a way as to expand laterally (i.e. along at least one direction parallel with the plane defined by the flexible unitary layer 44).

Figure 9:
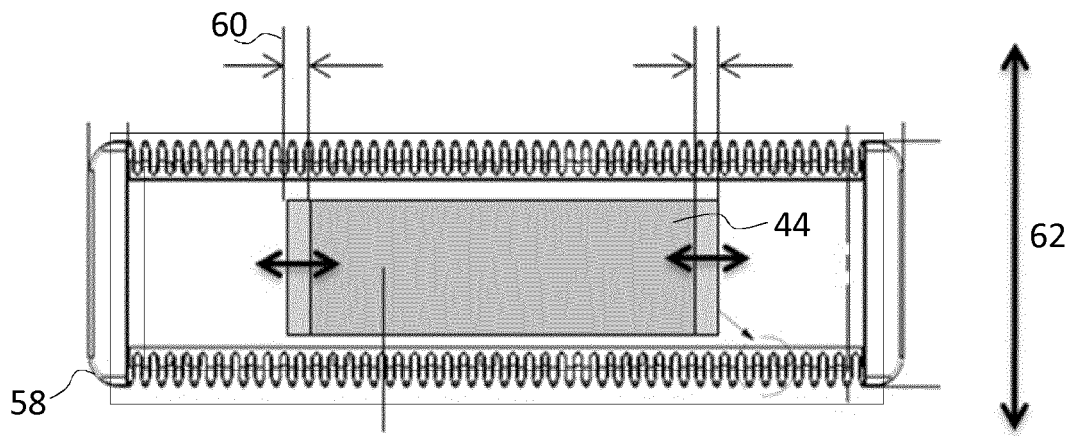
FIG. 9 schematically depicts an underside view of a first example friction control device as incorporated within a shaver head.
Figure 10:
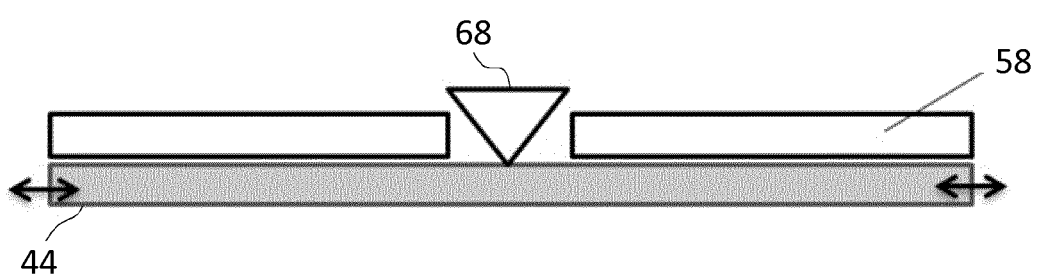
FIG. 10 schematically depicts a cross-sectional view of the first example friction control device.

By way of illustration, FIG. 9 shows an aerial (underside) view of an EAP unitary flexible layer 44 as incorporated within a shaver trimmer head 58. FIG. 10 shows a (side) cross-sectional view of the same EAP layer 44. A shaver trimmer head, when in use, may generally undergo significant global motion as it is slid over a large area of skin. For the purposes of the present example, it is assumed that the global motion of the shaver head follows the bi-directional arrow 62.

In operation, the EAP layer 44 is electrically stimulated to deform in-plane to generate a lateral outwards expansion along one direction. By 'one direction' is meant along one dimension, wherein the layer may in fact expand in both positive and negative directions along this dimension, as indicated in FIG. 9. The expansion may in examples be parallel or perpendicular to the global gliding direction 62, depending for instance upon the form factor of the device. For the example of FIGS. 9 and 10, the expansion is shown as being perpendicular to the global gliding direction.

Optionally, the EAP layer may be provided having rounded edges, or may be curved, so as to prevent (out-of-plane) locking of edges of the EAP layer against for instance hairs, skin irregularities or bow waves in the human tissue receiving surface 18.

In-plane expansion of the EAP layer induces a state of slip across the receiving surface, thereby enabling global sliding or gliding of the shaver head to take place across an interface exhibiting significantly reduced static friction. According to particular examples, the expansion of the layer 60 on either side may be between approximately 100-500 μm. These figures are given purely by way of illustration and are not necessary for fulfillment of the embodiment.

According to examples, the EAP layer 44 may be stimulated to deform upon onset of global motion. The friction control device may in this case further comprise a sensor for sensing the onset of motion, and a controller adapted to respond to sensing signals generated by the sensor by stimulating the EAP layer 44 to expand. Suitable sensors include, by way of example only, accelerometers, light sensors and/or pressure sensors.

According to further examples, the EAP layer 44 may be stimulated to deform cyclically or periodically in time, i.e. to vibrate or oscillate at a given frequency. Suitable frequencies may include—by way of example only—low frequencies of between 1-5 Hz, preferably between 1-2 Hz. There may be provided in this case a controller configured to apply time-periodic electrical stimulation to the EAP layer 44 at a suitable frequency to induce the vibration.

FIG. 10 shows a side cross-sectional view of the friction control device. The EAP layer 44 is mounted within a low-friction linear support bearing structure 58. Fixing element 68 provides a coupling or fixing means, for fixing the EAP layer to the bearing structure. This element may be a part of linear support structure 58 or a separate element used to hold the two together.

The linear support structure prevents ant potential buckling of the EAP layer, both during and after deformation. Such a structure may however be avoided according to certain embodiments, by instead pre-straining the EAP layer and clamping or otherwise fixing each end with an elastic connection. Stimulating the EAP stretches the layer, but the layer remains in tension, reducing the risk of buckling.

Figure 11:
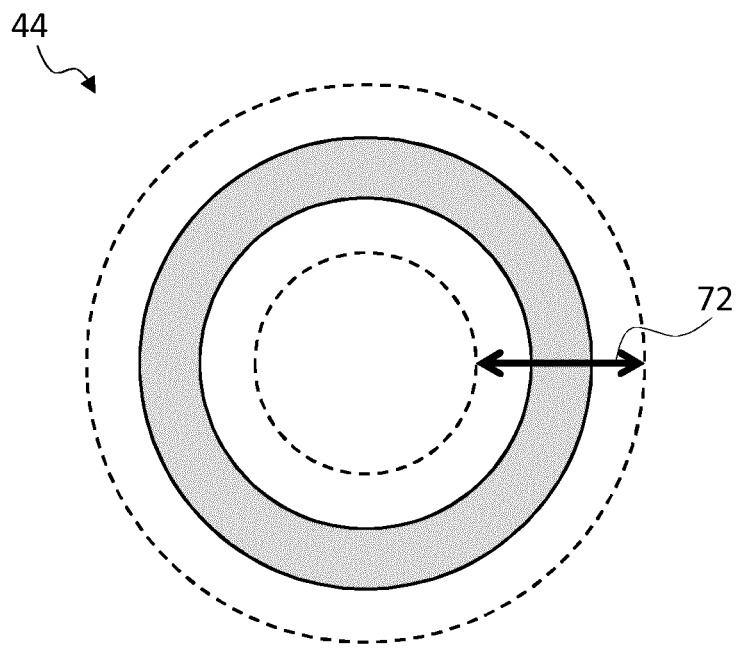
FIG. 11 schematically depicts an example flexible contact layer having annular shape.

Although in the example of FIGS. 9 and 10, a rectangular layer of electroactive polymer is used, in other examples, alternative shapes and forms of EAP layer may instead be used. FIG. 11 shows for instance an exemplary EAP layer having an annular shape. As shown by arrow 72, in this example, the annular EAP layer 44 is adapted to expand along a radial direction. Such a shape might be advantageous for instance for application within a rotary shaver comprising circular trimmer heads. The expansion 72 in this case may be adapted to be perpendicular to the circular motion of the trimmer blades, or to be either perpendicular or parallel with the global motion of the trimmer head over a user's skin.

Figure 12:
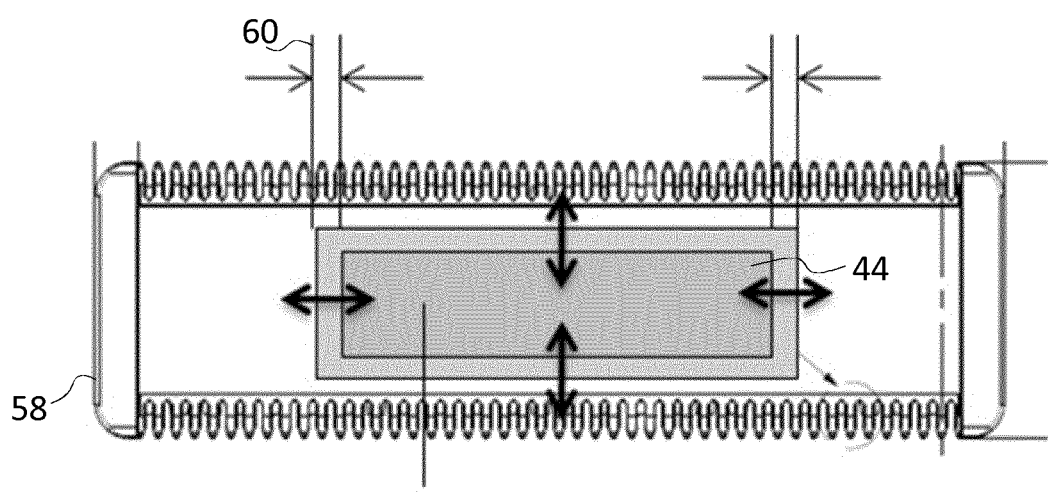
FIG. 12 schematically depicts a second example friction control device as incorporated within a shaver head.

FIG. 12 shows a second example of an EAP layer 44 as incorporated within a shaver-head 58. This example is functionally similar to the example of FIGS. 9 and 10, but comprises an EAP layer adapted to undergo in-plane expansion in two orthogonal directions. Bi-directional expansion may provide improved efficacy compared with one-way expansion since certain locking surface features, such as hairs or skin-lines, may be insensitive to expansion in only one direction.

Materials suitable for the EAP layer are known. Electroactive polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-tri-fluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to:
  acrylates, polyurethanes, silicones.

The sub-class conjugated polymers includes, but is not limited to:
  polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behavior under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behavior of the EAP layer in response to an applied electric field.

The EAP layer of each unit may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating. The use of an EAP to provide an expanding layer as shown in the examples of FIGS. 3 and 4 is not essential. According to at least one set of alternative examples, an expanding layer may be provided comprising a different variety of responsive material. Other examples of responsive materials include shape-memory alloys which have the property of deforming to adopt a particular memory shape in response to the application of a thermal stimulus. In examples, a thermal stimulus may be applied by means of a dedicated heating element, or may be achieved by Joule heating, through direct application of a current to the shape memory alloy.

Other examples include: magnetic shape change materials, adapted to deform in response to the application of certain magnetic stimuli; photomechanical materials, adapted to change shape in response to changing light levels; and pH sensitive polymers. A variety of other materials will also be readily known and understood by the skilled person in this field, each being adapted to deform in response to the application of any of an electronic, magnetic or electromagnetic stimulus.

The concept of the invention as embodied by the illustrative example of FIGS. 9-12 is not necessarily limited to the use of responsive materials to facilitate expansion of the unitary flexible layer 44. According to at least one set of alternative examples, a unitary flexible layer may be provided in combination with an arrangement of mechanical actuators, configured to manipulate the layer to induce a strain across it in a direction parallel with a plane defined by the layer.

Figure 13:
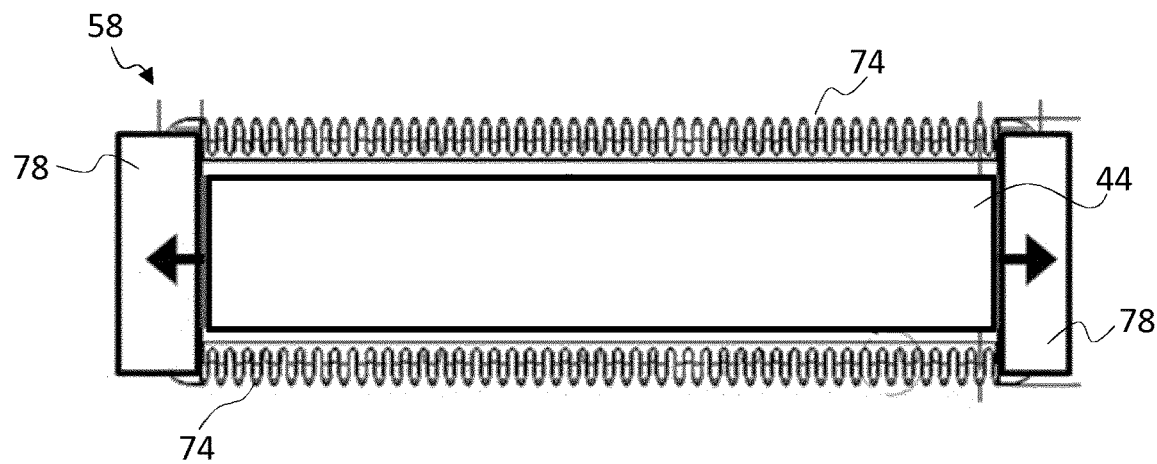
FIG. 13 schematically depicts a third example friction control device as incorporated within a shaver head, the device comprising an arrangement of external actuators.

One example of such an embodiment is shown in FIG. 13, which schematically illustrates an example friction control device as incorporated within the head 58 of a shaver device. The friction control device comprises a passive elastic layer 44 situated in between two parallel rows of trimmer blades 74. The elastic layer 44 is coupled at each end to a respective external actuator element 78. The actuator elements are operable to apply respective opposing lateral forces at each of the passive elastic layer 44, to thereby induce a stretching of the layer across a lateral direction.

In further examples, the actuators 78 may be operable to apply forces in two directions each, to thereby induce a bi-directional shear strain across the layer (two orthogonal directions parallel to the plane defined by the layer).

More than two actuators 78 may in further examples be provided in order to induce a strain in multiple in-plane directions.

The external actuators may consist of mechanical or mechatronic actuators, or may consist of actuating members comprising a responsive material adapted to deform in response to a stimulus in such a way as to apply opposing outwards forces to the layer 44 and induce a lateral shear strain.

According to further examples still, the external actuators 78 may be replaced or incorporated within an energy transmission mechanism adapted to harness kinetic energy generated or embodied by the shaver blades 74 in order to induce the lateral stretching of the layer 44.

Suitable materials for the passive elastic layer 44 include (by way of example only) silicone elastomer materials having a low friction surface texture, or textile materials having combined properties of stretchability and low surface friction.

In each of the embodiments described above, a contact surface arrangement has been provided as comprised by a single unitary surface 44, which is adapted to expand or to be expanded in order thereby induce a relative separation between the plurality of contact surface regions 40. However, according to a further set of examples, the plurality of contact surface regions may be provided by the contact surfaces of a plurality of distinct, spatially separated contact elements.

Figure 14:
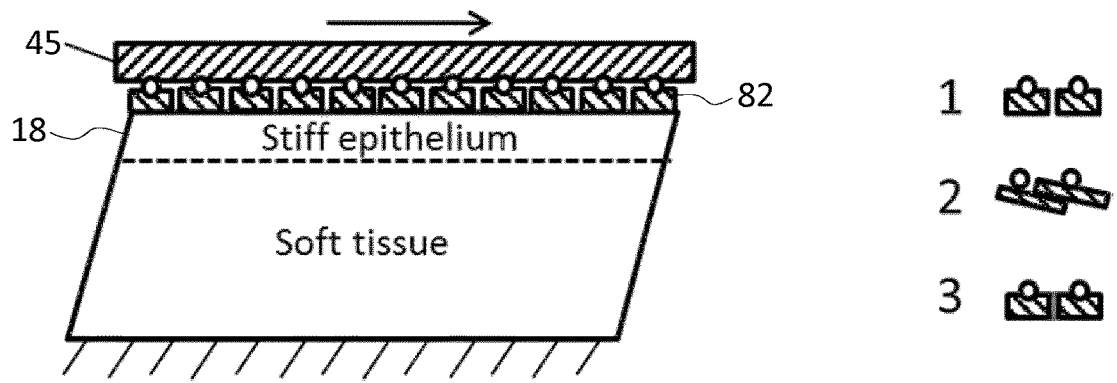
FIG. 14 schematically depicts a fourth example friction control device, comprising a plurality of distinct contact elements.

FIG. 14 shows one simple example of such an embodiment. The arrangement comprises an array of contact elements 82 which are mechanically coupled to a lower major surface of a flexible layer 45. Each contact element 82 comprises a lower contact surface. The contact surfaces of the plurality of elements form the contact surface arrangement for the device.

The layer 45 is adapted to be expanded—either by means of an arrangement of external actuators (not shown), or by means of a responsive material incorporated within the layer—so as to induce an in-plane strain along at least one direction of the layer. The strain causes a relative separation of the mechanically coupled contact elements 82, and hence a separation of the plurality of contact surfaces of the elements 82.

The elements 82 may be very small, micro-sized elements. This may increase the shear strain at the interface between the elements and a human tissue receiving surface.

As shown on the right hand side of FIG. 14, the plurality of contact elements may be arranged according to a number of different configurations. In particular, the contact elements 82 may 1) be arranged such that a small spatial separation is maintained between them, even when the flexible layer is not expanded; 2) be arranged such that the elements are able to move or slide over one another to some extent; or 3) be arranged having a compliant connection between them which strains with the relative movement of the elements.

The advantage of an arrangement comprising multiple contact elements is the large degree of choice in the material properties of the skin-contacting materials. For instance hydrophilic or hydrophobic materials may be used, or materials with a specific surface finish.

Although the arrangement of FIG. 14 shows the plurality of contact elements coupled to an expanding, flexible layer, the elements may according to other examples be mechanically mounted such that they can move relative to one another. This may make arrangement (2) more feasible.

Figure 15:
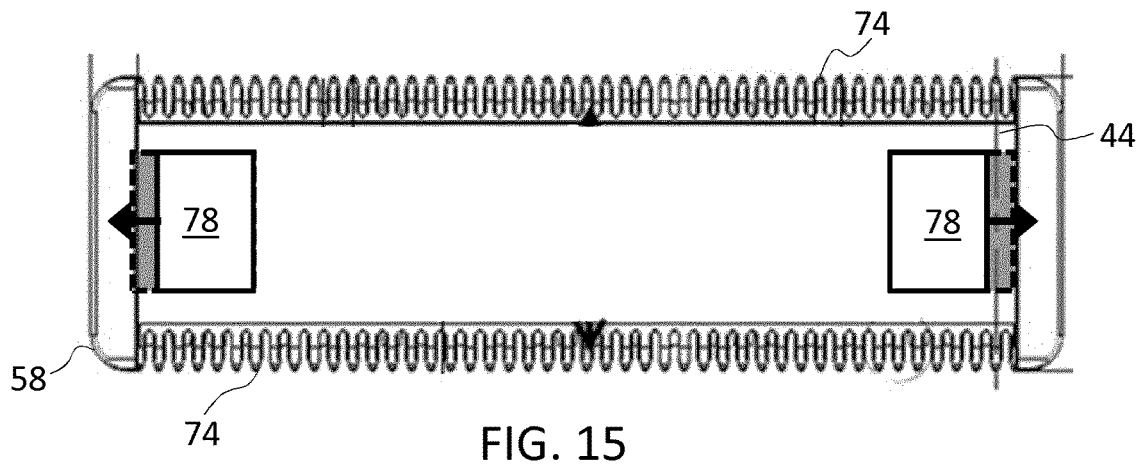
FIG. 15 schematically depicts a fifth example friction control device as incorporated within a shaver head.

In accordance with a further set of embodiments, there may be provided a friction control device comprising an assembly of two expanding surface elements, configured to expand in concert in order to induce a stain within a human tissue contact region. FIG. 15 shows an example of such an arrangement.

In the examples above in which an expanding (unitary) layer 44 is utilised, the expansion of the human tissue is induced by use of a single expanding element only. However, for very many applications, it may be necessary or desirable to induce strain across a relatively large area of human tissue. In such a case, a single expanding element 44 may be impractical, ineffective, or undesirably costly. This is especially the case for embodiments utilising an EAP expanding layer.

Additionally, the larger a single expanding layer becomes, the greater the normal force with which it is necessary to apply the expanding layer to the human tissue surface in order to maintain effective contact. This in turn increases the necessary tensile force required to be induced across the expanding layer in order to stretch the skin beneath. These factors may increase both the complexity of operation of the device (since it is difficult to maintain such a force evenly over such a wide area) and also the risk of incurring skin irritation or damage.

In order to overcome these problems, the embodiment illustrated by the example of FIG. 15 comprises an assembly of two expanding EAP elements 78, situated at each of two ends of a shaver head unit 58, in-between two sets of parallel cutting blades 74. Such an arrangement reduces the normal pressure being applied to the skin receiving surface to which the shaver is applied. It consequently also reduces the tensile force which it necessary to induce across the layers 78 in order to effect the expansion of the skin beneath.

There may further be provided in accordance with this embodiment a controller configured to provide synchronised control signals to the two expanding elements 78, so as to induce simultaneous and complementary expansion of the two elements (i.e. to ensure that the elements expand and shrink at the same time). Furthermore, the controller may control the applied signals so as to ensure the respective expansions of the two elements 78 are in opposing (i.e. complementary) directions.

For embodiments of the present invention, the main function of the product relies on the (local) manipulation of human tissue, or the actuation of tissue contacting interfaces. In such applications, EAP actuators for example provide unique benefits mainly because of the small form factor, the flexibility and the high energy density. Hence EAPs and photoresponsive polymers can be easily integrated in soft, 3D-shaped and/or miniature products and interfaces in order to provide the required friction control functionality.

The example of a shaver with an adaptive shaving head as described above is only one possible example. Other examples of such applications are:

Respiratory devices with a patient interface mask which has a responsive polymer based active cushion or seal, to provide reduced skin interference;

Consumer electronics devices or touch panels which provide local haptic feedback via an array of responsive polymer transducers which is integrated in or near the user interface;

Catheters with friction controlled surfaces, to provide smooth gliding of the catheter through anatomical cavities such as arteries or the digestive system.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A friction control device comprising:
a contact surface arrangement,
wherein the contact surface arrangement comprises a plurality of contact surface regions, and
wherein the plurality of contact surface regions are arranged to make contact with a receiving surface; and
an actuator assembly,
wherein the actuator assembly is adapted to control a separation of the plurality of contact surface regions in dependence upon an elasticity of the receiving surface and one or more surface properties of the receiving surface, and
wherein the extent of separation matches or exceeds that which can be applied to the receiving surface via the plurality of contact surface regions without static frictional forces across an interface between the friction control device and the receiving surface being overcome.

2. The friction control device as claimed in claim 1, wherein the actuator assembly is arranged to control the separation of the plurality of contact surface regions in dependence upon the coefficient of static friction between the plurality of contact surface regions and the receiving surface, and the modulus of elasticity of the receiving surface.

3. The friction control device as claimed in claim 1,
wherein the actuator assembly is arranged to control the separation between the plurality of contact surface regions so as to increase from a first separation distance to a second separation distance, and
wherein the ratio of the second separation distance to the first separation distance is between 1.001 and 1.01 or between 1.01 and 1.1.

4. The friction control device as claimed in claim 1,
wherein the plurality of contact surface regions are regions of a planar surface of a unitary flexible layer,
wherein the planar surface defines a plane, and
wherein the actuator assembly is arranged to induce a lateral strain across the unitary flexible layer in a direction parallel with the plane, thereby actuating a separation of the plurality of contact surface regions.

5. The friction control device as claimed in claim 4, wherein the actuator assembly comprises one or more responsive material components arranged to deform in response to an electrical, thermal, magnetic or electromagnetic stimulus.

6. The friction control device as claimed in claim 5,
wherein the one or more responsive material components are mechanically coupled to the unitary flexible layer, and
wherein the one or more responsive material components are arranged such that their deformation mechanically manipulates the unitary flexible layer to exhibit the lateral strain and consequently actuate a separation of the plurality of contact surface regions of the planar surface of the unitary flexible layer.

7. The friction control device as claimed in claim 4, wherein the actuator assembly comprises one or more mechanical actuators arranged to manipulate the unitary flexible layer to induce the lateral strain across it in the direction parallel with the plane defined by the unitary flexible layer.

8. The friction control device as claimed in claim 4, wherein the actuator assembly is arranged to induce the lateral strain across the unitary flexible layer in two orthogonal directions parallel with the plane.

9. The friction control device as claimed in claim 5,
wherein the one or more responsive material components are mechanically coupled to the unitary flexible layer,
wherein the actuator assembly is incorporated within the unitary flexible layer, and
wherein the unitary flexible layer is formed of a responsive material arranged and adapted to deform in response to an applied stimulus in order thereby to induce the lateral strain across the unitary flexible layer in one or more directions parallel with the plane, and consequently actuate a separation of the plurality of contact surface regions of the planar surface of the unitary flexible layer.

10. The friction control device as claimed in claim 4,
wherein the actuator assembly comprises one or more mechanical actuators arranged to manipulate the unitary flexible layer to induce the lateral strain across it in the direction parallel with the plane defined by the planar surface of the unitary flexible layer, and
wherein the actuator assembly comprises an energy transmission mechanism arranged to receive as input an external source of kinetic energy and to transfer the kinetic energy into the one or more mechanical actuators.

11. The friction control device as claimed in claim 1, wherein the plurality of contact surface regions comprises a plurality of spatially separated contact elements.

12. The friction control device as claimed in claim 11,
wherein the actuator assembly comprises a layer of a responsive material adapted to deform in response to an electrical, thermal, magnetic or electromagnetic stimulus,
wherein the deformation induces a lateral strain in the layer in a direction parallel with a plane defined by the layer, and
wherein the plurality of spatially separated contact elements are coupled to a surface of the layer such that the deformation of the layer induces a separation of the plurality of spatially separated contact elements.

13. The friction control device as claimed in claim 12, wherein the actuator assembly comprises one or more mechanical actuators arranged to physically manipulate the plurality of spatially separated contact elements in order to induce the separation between them.

14. The friction control device as claimed in claim 12, wherein the responsive material comprises an electroactive polymer material.

15. The friction control device as claimed in claim 1, further comprising a controller circuit adapted to control the actuator assembly to actuate a periodic separation between the plurality of contact surface regions, such that the periodic separation varies periodically over time.

16. A shaver or trimmer comprising a head portion for contacting a user's skin, the head portion comprising a friction control device as claimed in claim 1.

17. The friction control device as claimed in claim 1, wherein the actuator assembly is arranged to control the separation between the plurality of contact surface regions so as to increase from a first separation distance to a second separation distance, and wherein the ratio of the second separation distance to the first separation distance is greater than 1.1.

18. A method of controlling static friction across an interface between a contact surface arrangement and a receiving surface, the method comprising:
providing the contact surface arrangement, wherein the contact surface arrangement comprises a plurality of contact surface regions;
arranging the plurality of contact surface regions to make contact with the receiving surface; and
providing an actuator assembly to control a separation of the plurality of contact surface regions in dependence upon an elasticity of the receiving surface and one or more surface properties of the receiving surface, such that the extent of separation matches or exceeds that which can be applied to the receiving surface via the plurality of contact surface regions without static frictional forces across the interface being overcome.

\* \* \* \* \*